United States Patent [19]

Stern et al.

[11] Patent Number: 5,378,606
[45] Date of Patent: Jan. 3, 1995

[54] SPECIFIC DETECTION OF *NEISSERIA GONORRHOEAE*

[75] Inventors: Anne Stern, Penzberg; Karin Wolff, Germering, both of Germany

[73] Assignee: Boehringer Mannheim GmbH, Mannheim, Germany

[21] Appl. No.: 76,891

[22] Filed: Jun. 15, 1993

[30] Foreign Application Priority Data

Jun. 17, 1992 [DE] Germany .................. 4219821

[51] Int. Cl.$^6$ ............... C12Q 1/68; C12N 1/20; C12N 15/00; C07H 17/00
[52] U.S. Cl. .................. 435/6; 435/252.3; 435/320.1; 536/24.32
[58] Field of Search ............ 435/6, 252.3, 320.1; 536/24.32

[56] References Cited

U.S. PATENT DOCUMENTS 4,900,659  2/1990  Lo et al. .................. 435/6

FOREIGN PATENT DOCUMENTS 0452596  10/1991  European Pat. Off. .

Primary Examiner—Margaret Parr
Assistant Examiner—William Alexander
Attorney, Agent, or Firm—Nikaido, Marmelstein, Murray & Oram

[57] ABSTRACT

The present invention concerns a *Neisseria gonorrhoeae*-specific nucleic acid probe which has at least one of the nucleic acid sequences shown in SEQ ID NO 1-15 as well as a method for the detection of the pathogenic Neisseria species *N.gonorrhoeae* using such a nucleic acid probe. The sequences shown in Sequence ID Nos. 1-15 correspond to or are complementary to partial regions of the 23S rRNA gene or to the spacer region located on the 3' side thereof.

16 Claims, 1 Drawing Sheet

SPECIFIC DETECTION OF *NEISSERIA GONORRHOEAE*

The present invention concerns specific nucleic acid probes for the detection of the *Neisseria gonorrhoeae* pathogen as well as a method for the detection of *Neisseria gonorrhoeae* using these probes.

*N.gonorrhoeae* is the pathogen of gonorrhoea, a venereal disease which is one of the most frequent notifiable infectious diseases in the world. The number of infections alone is about 60-65 million every year (World Health Statisticals Annual, 1979; Herrmann, "Innere Medizin in Praxis und Klinik"; Hornbostel H., Kaufmann W., Siegenthaler W., eds., Thieme Verlag, 1985, 59-62). The symptoms depend on the sex of the carrier of the disease. While in men the genital infection manifests itself mainly as a purulent inflammation and swelling of the urethral orifice, in women inflammation of the cervix mainly occurs and sometimes also of the urethra. In women no or only slight symptoms occur in 50% of cases of infection. In 10 to 15% of women the infection spreads to the fallopian tubes which results in a risk of sterility. In 1 to 3% of cases a systemic invasion by the pathogen occurs in both sexes which can lead to arthritis, endocarditis and peritonitis. The course of the infections can often be asymptomatic and as a result many carriers contribute to the spread of the disease without themselves being recognizably affected by the disease (Davis et al., In: Microbiology, Harper International Edition 1981 p. 641-643).

The genus Neisseria is a group of closely related gram-negative diplococci which includes pathogenic as well as non-pathogenic species. Non-pathogenic Neisseria such as for example *Neisseria flava* and *elongata* colonize the mucous membranes of the cavity of the mouth, respiratory tract and genital tract and are a part of the normal microbial flora of man (Kayser, in: "Medizinische Mikrobiologie, Wiesmann E., ed., Thieme Verlag" 1986 104-144). The close relationship of Neisseria has inter alia been proven by DNA-DNA hybridization experiments (Hoke and Vedros, Int. J. System. Bacteriol. 31 (1982), 57-66). A prerequisite for a specific therapy and control of the spread of infection is a rapid and reliable detection method for the pathogen *N.gonorrhoeae* which can be used to efficiently and specifically detect *N.gonorrhoeae* and to unequivocally distinguish it from other species in particular from other members of the Neisseria genus.

The detection methods used up to now require the preparation of a culture. This causes problems in the transport of the material and during the culture since as a result of their autolytic enzyme systems, the gonococci are extremely sensitive to environmental influences such as change in temperature and dehydration. The culture of *N.gonorrhoeae* requires a selective medium (e.g. Thayer-Martin medium) on which, however, non-pathogenic Neisseria species, such as for example *N.lactamica*, can also grow. The definitive diagnostic test is therefore carried out by differentiating by means of carbohydrate usage, antigen detection, oxidase reaction or fluorescent antibody screening. All these test systems as well as the required culture of the microorganisms to be tested are very time-consuming and have to be mainly carried out in microbiological specialist laboratories.

Already several years ago it was recognized that it may be possible to specifically detect organisms using nucleic acid probes. Nucleic acid probes which are complementary to ribosomal RNA (rRNA) appear to be particularly suitable. These probes have the advantage that they are very sensitive since between 1000 copies and 10000 copies of this rRNA and also several copies of the gene (rDNA) coding for this rRNA are present in each cell.

Each cell has multiple rRNA operons which usually have the following structure in eubacteria: the 16S rRNA gene is located at the 5' end of the operon which is followed by the 23S rRNA gene; the 5S rRNA gene is located at the 3' end of the operon. The individual genes are separated from one another by spacer regions in which some of the transfer RNA (tRNA) genes and signal sequences for the post-transcriptional processing can be found. The rRNA operon is firstly transcribed into a single precursor RNA. Subsequently the primary transcript is then processed into the mature product by endoribonucleases and exoribonucleases. This means that the 23S rRNA sequences and the spacer regions are present as DNA in the genome as well as RNA transcripts.

The method of identifying organisms using such rRNA specific probes has already been described several times (EP-B 0 155 359, WO 84/02721, EP-A 0 076 123).

Probes whose sequences are complementary to partial regions of the rRNA (EP-A 0 272 009) have also been used for the detection of *Neisseria gonorrhoeae*. However, unequivocal test results could not be achieved using the probes described in EP-A 0 272 009. In addition the sensitivity of the detection when using these probes is inferior to that of the culture method (Panke et al., J. Clin. Microbiol. 29, (1991), 883-888).

Specific oligonucleotide probes for *Neisseria gonorrhoeae* are described in EP-A 0 408 077. These probes correspond to partial regions of the 16S rRNA of *Neisseria gonorrhoeae*. Nucleic acid probes which hybridize with the 23S rRNA of *Neisseria gonorrhoeae* were not described in EP-A 0 408 077. However, such probes are of interest since the length of the sequences allows a larger selection of specific probes.

Nucleic acid probes are described in WO 90/14442 which correspond to sequences of the 16S rRNA as well as to sequences from the 5' region of the 23S rRNA gene. However, in order to achieve a differentiation of the Neisseria species extremely stringent hybridization conditions have to be applied (hybridization in the presence of 0 9 mol/l NaCl at 60° C. washing in the presence of 0.03 mol/l NaCl at 60° C.). Some of the probes described in WO 90/14442 also hybridize with the non-pathogenic species *N.flava* even under these highly stringent conditions. The 23S rRNA-specific nucleic acid probes described in EP-A 0 337 896 also require highly stringent hybridization conditions and do not specifically hybridize even under these conditions with *N.gonorrhoeae* but also with other Neisseria species such as for example *N.meningitidis*. A nucleic acid probe from the spacer region between the 16S and 23S rRNA gene is proposed in EP-A 0 452 596 for the detection of *N.gonorrhoeae* which, however, also hybridizes with the nucleic acid of some strains of the non-pathogenic species *Neisseria cinerea*. These previously described 23S rRNA probes and rRNA spacer-specific probes are therefore not suitable for a specific detection of *N.gonorrhoeae*.

The object of the present invention was therefore to provide nucleic acid probes for *Neisseria gonorrhoeae* which have a high specificity and sensitivity under the usual hybridization conditions and thus enable a reliable qualitative and quantitative detection of this pathogen.

This object is achieved by a nucleic acid probe which is specific for Neisseria gonorrhoeae and which has at least one of the sequences shown in SEQ ID NO 1-15. The sequences of the oligonucleotides of the subgroup SEQ ID NO 1, 3, 5, 7, 9, 11, 13 correspond to partial regions of the 23S rRNA gene or to the spacer region located on the 3' side thereof. The sequences of the oligonucleotides of the subgroup SEQ ID NO 2, 4, 6, 8, 10, 12, 14 and 15 are complementary to these partial regions. The cellular rRNA or its precursor can only be detected in a direct hybridization preparation using the latter subgroup while the genomic DNA which codes for the corresponding RNA can be detected with both the subgroups.

The sequences of the said oligonucleotides are shown in Table 1:

TABLE I

| Designation | Nucleotide sequence | RDNA region* |
| --- | --- | --- |
| SEQ ID NO 1 | GCTGTGGGTAGGGGTGA | R |
| SEQ ID NO 2 | TCACCCCTACCCACAGC | R |
| SEQ ID NO 3 | CAGGTGGGTAGGATGAG | R |
| SEQ ID NO 4 | CTCATCCTACCCACCTG | R |
| SEQ ID NO 5 | GTAGGCTGATGAAGGT | R |
| SEQ ID NO 6 | ACCTTCATCAGCCTAC | R |
| SEQ ID NO 7 | ATCCGGGTTTTCTTAACA | R |
| SEQ ID NO 8 | TGTTAAGAAAACCCGGAT | R |
| SEQ ID NO 9 | ACAAGTCGGGCAGGTGC | R |
| SEQ ID NO 10 | GCACCTGCCCGACTTGT | R |
| SEQ ID NO 11 | GAAGGACTTCAAGAGAT | S |
| SEQ ID NO 11 | ATCTCTTGAAGTCCTTC | S |
| SEQ ID NO 13 | CGATTTGCAACAGTTTA | S |
| SEQ ID NO 14 | TAAACTGTTGCAAATCG | S |
| SEQ ID NO 15 | TTCTCGGTGTTAAGAAA | R |

*R: oligonucleotide corresponds to the 23S rRNA sequence
S: oligonucleotide corresponds to the spacer region Surprisingly it is possible to specifically detect Neisseria gonorrhoeae with the probes according to the present invention. Even under the less stringent hybridization conditions generally used (hybridization in the presence of 0.9 mol/l NaCl at 40° C., washing in the presence of 0.36 mol/l NaCl at 42°-60° C.) these probes do not hybridize with closely related Neisseria species such as e.g. N.flava and N.cinerea. The high specificity which results therefrom is therefore of great importance since apart from the pathogen N.gonorrhoeae, many non-pathogenic Neisseria species which are a component of the human mucous membrane can be present in the sample to be examined.

The probes according to the present invention are at least 14 nucleotides long. However, they can have further nucleotides, preferably up to 8 nucleotides, at their 5' and/or 3' end. However, a total length of 30 nucleotides should not be exceeded.

The present invention therefore also concerns a Neisseria gonorrhoeae-specific nucleic acid probe which has at least one of the sequences shown in SEQ ID NO 1-15 as well as further nucleotides, preferably up to 8 further nucleotides, at its 5' and/or 3' end.

The additional nucleotides of the probe can in this case be any desired nucleotides, however, those nucleotides are preferred which correspond to the nucleotides present on the rDNA at the 5' or at the 3' end or to their complementary nucleotides.

The nucleic acid probes specific for N.gonorrhoeae according to the present invention can be present in various forms: as single-stranded oligonucleotides or as double-stranded oligonucleotide fragments, associated with other sequences which have no homology to the DNA or RNA of Neisseria gonorrhoeae such as for example cloning vectors. When using double-stranded probes it is essential to denature the probe before carrying out the actual test reaction. The nucleic acid probes according to the present invention can contain modified as well as unmodified ribonucleotides and/or deoxyribonucleotides. Single-stranded vectors such as M13 and also double-stranded vectors such as pBR322 and its derivatives can be used to clone these nucleic acid probes. Furthermore the sequences of the probes listed in Table 1 can be coupled together so that two or more probes are for example present in one vector.

The present invention also concerns a nucleic acid probe which is specific for Neisseria gonorrhoeae which is characterized in that it contains one or several copies of the sequences shown in SEQ ID NO 1-15 cloned in a single-stranded or double-stranded vector.

In a preferred embodiment of the present invention the nucleic acid probes are labelled. All types of labelling known to a person skilled in the art are suitable for this such as incorporation of radioactive isotopes or the incorporation of a non-radioactive label such as for example a digoxigenin-coupled nucleotide which can be detected by means of an enzymatically-labelled or fluorescent-labelled antibody.

In addition the present invention concerns a method for the detection of N.gonorrhoeae by hybridizing DNA or of the sample to be examined with at least one probe according to the present invention under the usual hybridization conditions and detecting the hybrid formation.

The nucleic acid probes according to the present invention hybridize with the rRNA as well as with the corresponding rRNA genes on the bacterial genome. It is therefore possible in the method according to the present invention to determine the presence and absence of N.gonorrhoeae quantitatively and qualitatively via both nucleic acid types.

The detection via hybridization with at least one of the probes according to the present invention is carried out according to the usual methods for the detection of nucleic acids via hybridization (Southern, J. Mol. Biol. 98, 1975, 503). All known hybridization variants such as solid phase hybridization, hybridization in solution, sandwich hybridization, two-component hybridization can be used. The detection is carried out in the usual way by means of a radioactive or non-radioactive labelling of the probe.

The invention is elucidated further by the following examples in conjunction with the sequence protocols 1-15 which show the nucleic acid probes according to the present invention and FIG. 1 which shows a non-radioactive detection of Neisseria gonorrhoeae.

Example 1

The preparation of bacterial chromosomal DNA of the species listed below is carried out according to the protocol described by Stern et al. (Cell 37 (1984), 447).

The chromosomal DNA (250 ng in each case) of the following species is applied to a nitrocellulose filter using a slot-blot apparatus:
pathogenic Neisseria species:
  Neisseria gonorrhoeae
  Neisseria meningitidis
  non-pathogenic Neisseria species:

N.lactamica
N.mucosa
N.subflava
N.sicca
N.elongata
N.cinerea
N.flava
N.denitrificans For this the filters are moistened with 2×buffer (2×buffer: 2 mol/l NaCl, 50 mmol/l Tris-HCl, pH 7.5 and 1 mmol/l EDTA), clamped and a vacuum is applied. 50 µl 50 mmol/l Tris-HCl, pH 7.5, 5 mmol/l EDTA is added to the DNA (concentration 0.1–1 µg/l) and boiled for 3 minutes for the denaturation. Subsequently the mixture is immediately transferred onto ice, 50 µl 2×buffer is added and this solution is pipetted into the slots of the slot-blot apparatus. The slots are rinsed with 100 µl 1×buffer (2×buffer diluted with water 1:1), the filter is detached from the apparatus, air-dried and baked in a vacuum for 2 hours at 80° C.

Hybridization with the oligonucleotides according to the present invention is carried out in the usual manner. The nitrocellulose filters are firstly pre-hybridized for 2 hours in 1×VHP (Vorhybridisierungspuffer, pre-hybridizing buffer) (2×VHP: 0.1% bovine serum albumin, 0.1% Ficoll 400,000, 0.1% polyvinylpropylidone, 1% glycerol, 1.8 mol/l NaCl, 50 mmol/l Na₂HPO₄, 50 mmol/l NaH₂PO₄, 10 mmol/l EDTA and 10 mg/ml heat-denatured herring sperm DNA).

The VHP is removed for the hybridization and replaced by the ₃₂P-labelled oligonucleotide probe in hybridization buffer (HB) (HB: 1×VHP; sample is labelled with the random primed DNA labelling kit, Boehringer Mannheim GmbH, Catalogue No. 1004 760, according to the manufacturer's instructions). The hybridization is carried out in a hybridization oven at 40° C. The HB is heated to 80° C. before use. After a hybridization period of at least 6 hours the filters are washed in washing buffer (WB: 0.36 mol/l NaCl, 10 mmol/l Na₂HPO₄, 10 mmol/l NaH₂PO₄, 2 mmol/l EDTA, 0.05% SDS) at first twice at room temperature and then twice at 42° C. The washing temperature is increased to a maximum of 60° C. depending on the GC content of the sample. The actual maximum washing temperatures for the examined probes which allow an optimal discrimination of the species DNA are shown in Table II.

TABLE II

| Probe | Washing temperature (°C.) |
|---|---|
| SEQ ID NO 1 | 52 |
| SEQ ID NO 3 | 52 |
| SEQ ID NO 6 | 48 |
| SEQ ID NO 7 | 48 |
| SEQ ID NO 9 | 58 |
| SEQ ID NO 11 | 48 |
| SEQ ID NO 13 | 48 |

Subsequently the filters are exposed to an X-ray film in the usual way and evaluated.

The results of the hybridization of the various nucleic acid probes with pathogenic and non-pathogenic species are shown in Table III.

TABLE III

| Species* (strain/isolate No.) | | Probe (SEQ ID NO..) | | | | | |
|---|---|---|---|---|---|---|---|
| | | 1 | 3 | 6 | 7 | 9 | 11 | 13 |
| N. gonorrhoeae | MS11 | + | + | + | + | + | + | + |
| N. gonorrhoeae | r2 | + | + | + | + | + | + | + |
| N. gonorrhoeae | R16 | + | + | + | + | + | + | + |
| N. gonorrhoeae | r21 | + | + | + | + | + | + | + |
| N. gonorrhoeae | 510 | + | + | + | + | + | + | + |
| N. gonorrhoeae | 514 | + | + | + | + | + | + | + |
| N. meningitidis | B | − | − | − | − | − | − | − |
| N. meningitidis | C | − | − | − | − | − | − | − |
| N. meningitidis | D | − | − | − | − | − | − | − |
| N. meningitidis | 2-4 | − | − | − | − | − | − | − |
| N. meningitidis | 3-1 | − | − | − | − | − | − | − |
| N. lactamica | 1855 | − | − | − | − | − | − | − |
| N. lactamica | 3272 | − | − | − | − | − | − | − |
| N. mucosa | 112 | − | − | − | − | − | − | − |
| N. mucosa | 114 | − | − | − | − | − | − | − |
| N. subflava | 124 | − | − | − | − | − | − | − |
| N. sicca | 118 | − | − | − | − | − | − | − |
| N. sicca | 2844 | − | − | − | − | − | − | − |
| N. elongata | 129 | − | − | − | − | − | − | − |
| N. cinerea | 126 | − | − | − | − | − | − | − |
| N. cinerea | 2199 | − | − | − | − | − | − | − |
| N. flava | 122 | − | − | − | − | − | − | − |
| N. flava | 123 | − | − | − | − | − | − | − |
| N. denitrificans | 2950 | − | − | − | − | − | − | − |

*Classified according to Bergey's Manual of Systematic Bacteriology, Krieg N.R., Holt G., eds., Williams and Wilkins, Baltimore (1984), 288-298

In order to check the specificity of the nucleic acid probes the genomic DNA of non-Neisseria species (also including colonizers of the human mucous membrane) is incorporated as a further control in a second hybridization preparation.

The result of this hybridization is shown in Table IV.

TABLE IV

| Species* (strain/isolate No.) | | Probe (SEQ ID NO..) | | | | | |
|---|---|---|---|---|---|---|---|
| | | 1 | 3 | 6 | 7 | 9 | 11 | 13 |
| N. gonorrhoeae | R16 | + | + | + | + | + | + | + |
| N. gonorrhoeae | 514 | + | + | + | + | + | + | + |
| N. lactamica | 3272 | − | − | − | − | − | − | − |
| N. elongata | 129 | − | − | − | − | − | − | − |
| N. sicca | 2844 | − | − | − | − | − | − | − |
| N. cinerea | 2199 | − | − | − | − | − | − | − |
| N. denitrificans | 2950 | − | − | − | − | − | − | − |
| Moraxella bovis | D1931 | − | − | − | − | − | − | − |
| E. coli | GM 48 | − | − | − | − | − | − | − |
| Haemophilus influenzae | 2214 | − | − | − | − | − | − | − |
| Haemophilus parainfluenzae | 1207 | − | − | − | − | − | − | − |
| Proteus vulgaris | 770 | − | − | − | − | − | − | − |
| Pseudomonas putida | 574 | − | − | − | − | − | − | − |
| Bacillus alvei | 3006 | − | − | − | − | − | − | − |
| Leuconostoc mesenteroides | 83 | − | − | − | − | − | − | − |
| Listeria monocytogenes | ½a | − | − | − | − | − | − | − |
| Staphylococcus aureus | D1901 | − | − | − | − | − | − | − |
| Staphylococcus epidermidis | 1050 | − | − | − | − | − | − | − |
| Streptococcus pneumoniae | 3028 | − | − | − | − | − | − | − |
| Steptomyces griseus | A | − | − | − | − | − | − | − |
| Isolate from a mouth swab | | − | − | − | − | − | − | − |

Example 2

Non-radioactive detection of *Neisseria gonorrhoeae*

For a non-radioactive detection of *Neisseria gonorrhoeae* firstly a specific DNA fragment is amplified by means of a polymerase chain reaction in which the fragments are at the same time labelled by incorporation of DIG-11-dUTP. These labelled fragments are then added to oligonucleotides which can hybridize with these fragments and thus act as a capture probe. The immobilization is then carried out by coupling the 3' ends of these oligonucleotides to biotin by which means these oligonucleotides are bound to a microtitre plate coated with streptavidin. Unspecific PCR fragments which cannot hybridize with the oligonucleotide acting as a capture probe are removed in subsequent washing steps. The detection of the bound specific DNA fragments is carried out by means of the digoxigenin label after addition of a POD-conjugated antibody peroxidase conjugated antibody against digoxigenin and ABTS ® substrate (2,2'-azino-di-[3-ethyl-benzthiazoline sulfonate]) solution for the peroxidase reaction. Binding of the amplified DNA fragment to the capture probe can then be detected via conversion of the substrate which can be measured in a photometer (see FIG. 1).

In order to carry out the experiment, the wells of a 96-well microtitre plate are firstly coated at 4° C. overnight with streptavidin (100 µl of a solution of 1 µg/ml in PBS) according to EP-A 0 344 578 and unspecific binding sites which are still free are blocked by incubation with 300 µl BSA (10 mg/ml bovine serum albumin) for 2 hours at room temperature.

The oligonucleotides SEQ ID NO 1 and 15 are selected as PCR primers for the amplification of a specific DNA fragment from the chromosomal gonococcal DNA. The hybridization of these primers is carried out at a temperature of 57° C. The subsequent PCR is carried out in the usual way. The product obtained in this way has a length of 750 bp. In order to denature the DNA fragments, 20 µl TE buffer and 10 µl 0.5 mol/l NaOH are added to 20 µl of the amplification mixture and incubated for 10 minutes at room temperature. This denaturation mixture is neutralized by addition of 450 µl acidified hybridization solution (50 mmol/l Na phosphate buffer, pH 6.8, 0.05 mol/l HCl, 0.75 mol/l NaCl, 75 mmol/l Na citrate, 0.05% BSA, pH 5.4). The biotin-labelled oligonucleotide (100 ng/ml; capture probe, SEQ ID NO 5) is added to this solution. 200 µl of this hybridization mixture is added to microtitre plates coated with streptavidin and incubated for 3 hours at 37° C. The DNA fragment is bound to the streptavidin-coating of the microtitre plate via the biotin-labelled oligonucleotide. Subsequently the plates are washed three times with 0.9% NaCl solution, then 200 µl conjugate solution (200 mU/ml <DIG>-polyPOD conjugate (Fab:POD=1:1) in 100 mmol/l Tris/HCl, pH 7.5, 0.9% NaCl, 1% BSA) is added and it is incubated for 30 minutes at 37° C. After washing three times with 0.9% NaCl solution, the substrate reaction is started by addition of 200 µl ABTS ® substrate solution (2,2'-azino-di-[3-ethyl-benzthiazoline sulfonate](1.9 mmol/l)) (ABTS ®: Boehringer Mannheim GmbH, Catalogue No. 756407 in ABTS ® buffer: Boehringer Mannheim GmbH, Catalogue No. 1204530). After incubating for 5–15 min at 37° C., the change in colour is measured at 405 nm in a photometer (Easy Reader EAR 400 FW microtitre plate reader, SLT-Labinstruments, Groedig/Salzburg).

The probes and vectors described in this application can be prepared according to the method described in U.S. Pat. No. 5,173,401 which is essentially equivalent to EP 0 408 077 cited on page 4, line 8. In addition, the claimed probes can be obtained by chemical synthesis as described in T. Brown and D. J. S. Brown, *Modern Machine Aided Methods of Oligodeoxynucleotide Synthesis*, which can be found in *Oligonucleotides and Analogues, A Practical Approach*, ed. F. Eckstein, IRL press, 1991, pp.1–24. The parts of U.S. Pat. No. 5,173,401 and T. Brown and D. J. S. Brown, *Modern Machine Aided Methods of Oligodeoxynucleotide Synthesis* which are directed to the preparation of vectors and probes are herein incorporated by reference.

---

Figure 1:
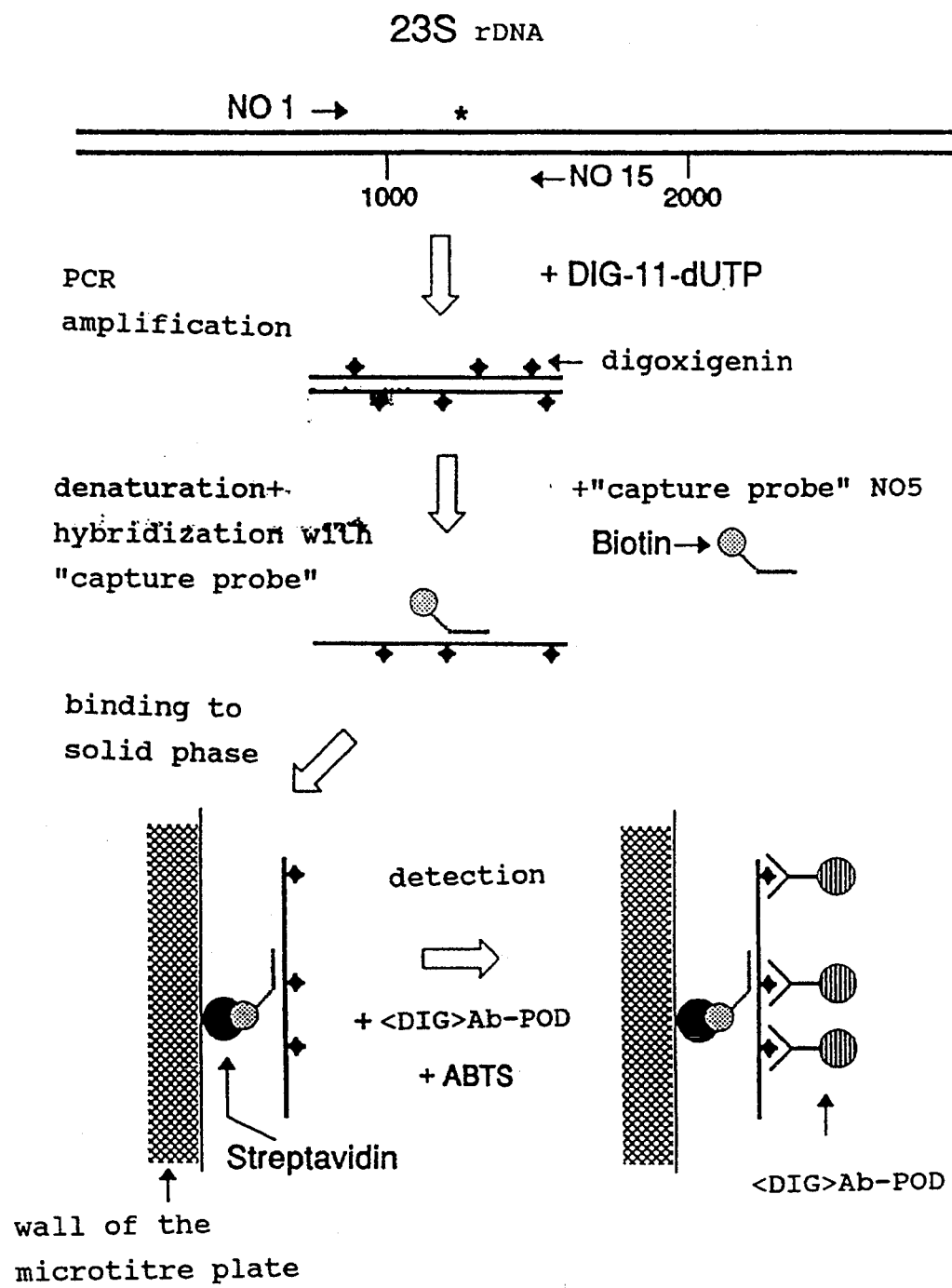
FIG. 1 shows a nonradioactive method of detecting *Neisseria gonorrhoeae*.

We claim:

1. A nucleic acid probe for the detection of *Neisseria gonorrhea*, wherein said probe comprises a sequence selected from the group consisting of the sequences shown in SEQ ID NOS: 4 to 15 inclusive, wherein any additional nucleotides which are present in the probe do not change the specific hybridization of said probe and wherein the total length of said probe is at least 14 nucleotides but less than 30 nucleotides.

2. The probe according to claim 1, wherein less than 8 additional nucleotides are at the 5' end, the 3' end or at both the 5' and the 3' ends.

3. The probe according to claim 1, wherein any additional nucleotides present correspond to nucleotides present in a natural 23S rRNA gene from which the probes are derived.

4. The probe according to claim 1, wherein said probe comprises labeled, and nonlabeled or both labeled and nonlabeled ribonucleotides or deoxyribonucleotides.

5. The probe according to claim 1, wherein said probe is labeled.

6. The probe according to claim 5, wherein said probe is radioactively labeled.

7. The probe according to claim 5, wherein said probe is nonradioactively labeled.

8. The probe according to claim 1 wherein said probe is single stranded.

9. The probe according to claim 1 wherein said probe is double stranded.

10. A cloning vector containing the probe according to claim 1.

11. The cloning vector according to claim 10, wherein said cloning vector is single stranded.

12. The cloning vector according to claim 10, wherein said cloning vector is double stranded.

13. The vector according to claim 10, wherein said cloning vector contains more than one copy of said probe.

14. The vector according to claim 10, wherein said cloning vector contains two or more probes.

15. A method for the detection of *Neisseria gonorrhea*, comprising the steps of:

hybridizing a probe containing a sequence selected from the group consisting of the sequences shown in SEQ ID NOS: 4 to 15 inclusive, wherein any additional nucleotides which are present do not change the specific hybridization of said probe and wherein the total length of said probe is less than 30 nucleotides, with a sample containing DNA or RNA, and detecting any hybrid formation wherein said detection of hybridization indicates the presence of *Neisseria gonorrhea*.

16. The method according to claim 15, wherein said probes are labeled.

* * * * *

SEQUENCE LISTING ( 1 ) GENERAL INFORMATION:

( i ) APPLICANT: STERN, Anne
                   WOLFF, Karin ( i i ) TITLE OF INVENTION: SPECIFIC DETECTION OF NEISSERRIA GONORRHOEAE ( i i i ) NUMBER OF SEQUENCES: 15

( 2 ) INFORMATION FOR SEQ ID NO: 1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: CDNA to RRNA ( x i ) SEQUENCE DESCRIPTION: SEQ ID NO: 1:

GCTGTGGGTA GGGGTGA        17

( 2 ) INFORMATION FOR SEQ ID NO: 2:

( i ) SEQUENCE CHARACTERISTICS:
        ( A ) LENGTH: 17 base pairs
        ( B ) TYPE: nucleic acid ( C ) STRANDEDNESS: single
            ( D ) TOPOLOGY: linear ( i i ) MOLECULE TYPE: CDNA to RRNA ( x i ) SEQUENCE DESCRIPTION: SEQ ID NO: 2:

TCACCCCTAC CCACAGC                                                                                          17

( 2 ) INFORMATION FOR SEQ ID NO: 3:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: CDNA to RRNA ( x i ) SEQUENCE DESCRIPTION: SEQ ID NO: 3:

CAGGTGGGTA GGATGAG                                                                                          17

( 2 ) INFORMATION FOR SEQ ID NO: 4:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: CDNA to RRNA ( x i ) SEQUENCE DESCRIPTION: SEQ ID NO: 4:

CTCATCCTAC CCACCTG                                                                                          17

( 2 ) INFORMATION FOR SEQ ID NO: 5:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: CDNA to RRNA ( x i ) SEQUENCE DESCRIPTION: SEQ ID NO: 5:

GTAGGCTGAT GAAGGT                                                                                           16

( 2 ) INFORMATION FOR SEQ ID NO: 6:

( i ) SEQUENCE CHARACTERISTICS:
            ( A ) LENGTH: 16 base pairs
            ( B ) TYPE: nucleic acid
            ( C ) STRANDEDNESS: single
            ( D ) TOPOLOGY: linear ( i i ) MOLECULE TYPE: CDNA to RRNA ( x i ) SEQUENCE DESCRIPTION: SEQ ID NO: 6:

ACCTTCATCA GCCTAC                                                                                           16

( 2 ) INFORMATION FOR SEQ ID NO: 7:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: CDNA to RRNA ( x i ) SEQUENCE DESCRIPTION: SEQ ID NO: 7

ATCCGGGTTT TCTTAACA                                                                                          18

(2) INFORMATION FOR SEQ ID NO: 8:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: CDNA to RRNA (xi) SEQUENCE DESCRIPTION: SEQ ID NO: 8:

TGTTAAGAAA ACCCGGAT                                                                                          18

(2) INFORMATION FOR SEQ ID NO: 9:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: CDNA to RRNA (xi) SEQUENCE DESCRIPTION: SEQ ID NO: 9:

ACAAGTCGGG CAGGTGC                                                                                           17

(2) INFORMATION FOR SEQ ID NO: 10:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: CDNA to RRNA (xi) SEQUENCE DESCRIPTION: SEQ ID NO: 10:

GCACCTGCCC GACTTGT                                                                                           17

(2) INFORMATION FOR SEQ ID NO: 11:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: CDNA to rRNA (xi) SEQUENCE DESCRIPTION: SEQ ID NO: 11:

GAAGGACTTC AAGAGAT                                                                                           17

(2) INFORMATION FOR SEQ ID NO: 12:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: CDNA to RRNA (xi) SEQUENCE DESCRIPTION: SEQ ID NO: 12:

ATCTCTTGAA GTCCTTC                                                                                           17

(2) INFORMATION FOR SEQ ID NO: 13:

(i) SEQUENCE CHARACTERISTICS:

-continued (A) LENGTH: 17 base pairs
(B) TYPE: nucleic acid
(C) STRANDEDNESS: single
(D) TOPOLOGY: linear (ii) MOLECULE TYPE: CDNA to RRNA (xi) SEQUENCE DESCRIPTION: SEQ ID NO: 13:

CGATTTGCAA CAGTTTA  17

(2) INFORMATION FOR SEQ ID NO: 14:

(i) SEQUENCE CHARACTERISTICS:
(A) LENGTH: 17 base Pairs
(B) TYPE: nucleic acid
(C) STRANDEDNESS: single
(D) TOPOLOGY: linear (ii) MOLECULE TYPE: CDNA to RRNA (xi): SEQUENCE DESCRIPTION: SEQ ID NO: 14:

TAAACTGTTG CAAATCG  17

(2) INFORMATION FOR SEQ ID NO: 15:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: CDNA to RRNA (xi) SEQUENCE DESCRIPTION: SEQ ID NO: 15:

TTCTCGGTGT TAAGAAA  17